United States Patent [19]

Beyer et al.

[11] Patent Number: 6,127,367
[45] Date of Patent: Oct. 3, 2000

[54] METHOD OF REDUCING TISSUE DAMAGE ASSOCIATED WITH NON-CARDIAC ISCHEMIA

[75] Inventors: Thomas A. Beyer, Old Lyme; Delvin R. Knight, Jr., Ledyard; Banavara L. Mylari, Waterford; Peter J. Oates, Gales Ferry; E. Roy Pettipher, Norwich; W. Ross Tracey, Niantic, all of Conn.

[73] Assignee: Pfizer, Inc., New York, N.Y.

[21] Appl. No.: 08/803,301

[22] Filed: Feb. 20, 1997

Related U.S. Application Data

[60] Provisional application No. 60/012,707, Feb. 29, 1996.

[51] Int. Cl.$^7$ .......................... A61K 31/495; A61K 31/50
[52] U.S. Cl. ............................................................ 514/248
[58] Field of Search ............................................. 514/248

[56] References Cited

U.S. PATENT DOCUMENTS

| | | | |
|---|---|---|---|
| 4,492,706 | 1/1985 | Kallai-Sanfacon | 424/270 |
| 4,939,140 | 7/1990 | Larson et al. | 514/222 |
| 5,064,830 | 11/1991 | Going | 514/252 |
| 5,391,551 | 2/1995 | Peterson | 514/248 |
| 5,476,846 | 12/1995 | Lardy et al. | 514/79 |

FOREIGN PATENT DOCUMENTS

| | | |
|---|---|---|
| 0310931 | 12/1989 | European Pat. Off. . |
| 0485217 | 5/1992 | European Pat. Off. . |
| 0745600 | 4/1996 | European Pat. Off. . |
| WO9619225 | 6/1996 | WIPO . |

OTHER PUBLICATIONS

CA 111:91114, Yasuda et al, 1989.

Ronald G. Tilton, et al., Diabetes, Vo. 44, Feb. 1995, "Effects of Vascular and Neural Dysfunction in Streptozocin–Induced Diabetic Rats".

Mylari B.L., et al., "Novel, potent aldose reductase inhibitors: 3,4–dihydro–4–oxo–3–([5–trifuoromethyl)–Z–benzothiazolyl] methyl–1–phthalazineacetic acid (zopolrestat) and congeners", J. Med Chem 1991 Jan.; 34 (1): 108–22.

Hosotani, H., et al., "Effects of topical aldose reductase inhbitor CT–112 on corneal sensitivity of diabetic rats", Curr–Eye–Res., 1996 Oct.; 15 (10): 10005–7.

G. Said, *Neuropathies Metaboliques, 1. Diabetic Neuropathies*, vol. 141, Rev. Neurol (Paris), No. 11, pp. 683–693, 1985.

David E. Price, et al., *Effect of aldose Reductase Inhibition on Resistance to Ischemic Conduction Block in Diabetic Subjects*, vol. 14 No. 5, Diabetes Care, pp. 411–413, May 1991.

Hitoshi Yasuda, et al., *Effect of Prostaglandin $E_1$ Analogue TFC 612 on Diabetic Neuropathy in Streptozocin–Induced Diabetic Rats*, vol. 38, Diabetes, pp. 832–838, Jul. 1989.

Walter De Gruyter, *Glomerukosklerose, diabetische, and Retinopathia diabetica*, Pschrymbel, Klinisches, Worterbuch, p. 552 and p. 1325, 257$^{th}$ edition, 1994.

Roger C. Bone, et al., *Gram–Negative Sepsis: A Dilemma of Modern Medicine*, Clinical Microbiology Reviews, Jan. 1993, pp. 57–68, 1993, vol. 6 No. 1.

Joseph R. Williamson, et al., *Hyperglycemic Pseudohypoxia and Diabetic Complicantions*, vol. 42, Diabetes, pp. 801–813, Jun. 1993.

*Primary Examiner*—Kimberly Jordan
*Attorney, Agent, or Firm*—Peter C. Richardson; Gregg C. Benson; A. Dean Olson

[57] ABSTRACT

A method of preventing non-cardiac tissue damage resulting from ischemia, comprising administering to a patient in need of such treatment an effective amount of an aldose reductase inhibitor.

18 Claims, No Drawings

METHOD OF REDUCING TISSUE DAMAGE ASSOCIATED WITH NON-CARDIAC ISCHEMIA

This is a continuation of provisional application U.S. Ser. No. 60/012,707 filed Feb. 29, 1996, the benefit of which is hereby claimed under 37 C.F.R. §1.78(a)(3).

FIELD OF THE INVENTION

This invention relates to the use of aldose reductase inhibitors to reduce tissue damage resulting from non-cardiac ischemia in mammals, including human patients.

BACKGROUND OF THE INVENTION

Aldose reductase inhibitors constitute a class of compounds which have become widely known for their utility in preventing and treating conditions arising from complications of diabetes such as diabetic neuropathy and nephropathy. Such compounds are well known to those skilled in the art and readily identified by standard biological tests.

For example, the compound zopolrestat, 1-Phthalazineacetic acid, 3,4-dihydro4-oxo-3-[[5-(trifluoromethyl)-2-benzothiazolyl]methyl]-, is known, for example from commonly assigned U.S. Pat. No. 4,939,140 to Larson et al., (the disclosure of which is hereby incorporated by reference) together with a number of compounds related thereto, to have utility as aldose reductase inhibitors. Zopolrestat has the structure

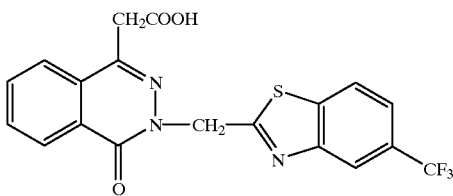

and, as an aldose reductase inhibitor, is useful in the treatment of the above-mentioned complications arising from diabetes mellitus.

Certain aldose reductase inhibitors have been taught for use in lowering lipid levels in mammals. See, for example, U.S. Pat. No. 4,492,706 (the disclosure of which is hereby incorporated by reference) to Kallai-sanfacon and EP 0 310 931 A2 (Ethyl Corporation).

Commonly assigned U.S. Pat. No. 5,064,830 (the disclosure of which is hereby incorporated by reference) to Going discloses the use of certain oxophthalazinyl acetic acids, including zopolrestat, for lowering of blood uric acid levels.

Commonly assigned U.S. application Ser. No. 08/059,688 discloses the use of certain aldose reductase inhibitors, including zopolrestat, for lowering blood lipid levels in humans. The disclosure notes that therapeutic utilities derive from the treatment of diseases caused by an increased level of triglycerides in the blood, such diseases include cardiovascular disorders such as thrombosis, arteriosclerosis, myocardial infarction, and angina pectoris.

Joseph R. Williamson et al., "Perspectives in Diabetes, Hyperglycemic Pseudohypoxia and Diabetic Complications", Diabetes, Vol. 42, 801–813, Jun., 1993 discloses that (FIG. 2) "Parallels between functional consequences of an increased systolic NADH/NAD$^+$ linked to hyperglycemic pseudohypoxia in diabetic tissues and hypoxia or ischemia in myocardial tissue."

SUMMARY OF THE INVENTION

This invention is directed to a method of reducing non-cardiac tissue damage (e.g., substantially preventing tissue damage, inducing tissue protection) resulting from ischemia. The method comprises administering to a mammal, including a human patient, in need of such treatment an amount of an aldose reductase inhibitor, preferably zopolrestat, effective at reducing non-cardiac tissue damage.

A preferred aspect of this invention is a method of reducing brain damage resulting from cerebral ischemia.

Yet another preferred aspect of this invention is a method of reducing liver damage resulting from hepatic ischemia.

Yet another preferred aspect of this invention is a method of reducing kidney damage resulting from renal ischemia.

Yet another preferred aspect of this invention is a method of reducing lung damage resulting from pulmonary ischemia.

Yet another preferred aspect of this invention is a method of reducing gastric damage resulting from gastric ischemia.

Yet another preferred aspect of this invention is a method of reducing intestinal damage resulting from intestinal ischemia.

Yet another preferred aspect of this invention is a method of reducing skeletal muscle damage resulting from skeletal muscle ischemia.

Yet another preferred aspect of this invention is a method of reducing spleen damage resulting from splenic ischemia.

Yet another preferred aspect of this invention is a method of reducing pancreas damage resulting from pancreatic ischemia.

Yet another preferred aspect of this invention is a method of reducing retinal damage resulting from retinal ischemia.

The term "reduction" is intended to include partial prevention or prevention which, although greater than that which would result from taking no drug or from taking placebo, is less than 100% in addition to substantially total prevention.

The term "damage resulting from [ . . . ] ischemia" as employed herein refers to conditions directly associated with reduced blood flow to non-cardiac tissue, for example due to a clot or obstruction of blood vessels which supply blood to the subject tissue and which result, inter alia, in lowered oxygen transport to such tissue, impaired tissue performance, tissue dysfunction and necrosis.

Those skilled in the art will recognize that this invention also includes improvement of tissue performance (e.g., the ability to sustain normal muscle function is enhanced during ischemia). For example, a human could walk a further distance before having to stop from skeletal muscle pain.

DETAILED DESCRIPTION OF THE INVENTION

Any aldose reductase inhibitor may be used as a compound (active agent) of this invention. The term aldose reductase inhibitor refers to compounds which inhibit the bioconversion of glucose to sorbitol catalyzed by the enzyme aldose reductase. Such inhibition is readily determined by those skilled in the art according to standard assays (J. Malone, Diabetes, 29:861–864, 1980. "Red Cell Sorbitol, an Indicator of Diabetic Control"). A variety of aldose reductase inhibitors are described and referenced below, however, other aldose reductase inhibitors will be known to those skilled in the art. The disclosures of U.S. patents listed below are hereby incorporated by reference. Also, common chemical USAN names or other designation are in parentheses where applicable, together with reference to appropriate patent literature disclosing the compound.

1. 3-(4-bromo-2-fluorobenzyl)-3,4-dihydro-4-oxo-1-phthalazineacetic acid (ponalrestat, U.S. Pat. No. 4,251,528);

2. N[[(5-trifluoromethyl)-6-methoxy-1-naphthalenyl]thioxomethyl}-N-methylglycine (tolrestat, U.S. Pat. No. 4,600,724);

3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);

4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);

5. 2R,4R-6,7-dichloro-4-hydroxy-2-methylchroman-4-acetic acid (U.S. Pat. No. 4,883,410);

6. 2R,4R-6,7-dichloro-6-fluoro-4-hydroxy-2-methylchroman-4-acetic acid (U.S. Pat. No. 4,883,410);

7. 3,4-dihydro-2,8-diisopropyl-3-oxo-2H-1,4-benzoxazine-4-acetic acid (U.S. Pat. No. 4,771,050);

8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);

10. (S)-6-fluorospiro[chroman-4,4'-imidazolidine]-2,5'-dione (sorbinil, U.S. Pat. No. 4,130,714);

11. d-2-methyl-6-fluoro-spiro(chroman-4',4'-imidazolidine)-2',5'-dione (U.S. Pat. No. 4,540,704);

12. 2fluoro-spiro(9H-fluorene-9,4'imidazolidine)2',5'-dione (U.S. Pat. No. 4,438,272);

13. 2,7-di-fluoro-spiro(9H-fluorene-9,4'imidazolidine)2',5'-dione (U.S. Pat. No. 4,436,745, U.S. Pat. No. 4,438,272);

14. 2,7-di-fluoro-5-methoxy-spiro(9H-fluorene-9,4$^1$imidazolidine)2$^1$,5$^1$-dione(U.S. Pat. No. 4,436,745, U.S. Pat. No. 4,438,272);

15. 7-fluoro-spiro(5H-indenol[1,2-b]pyridine-5,3'-pyrrolidine)2,5'-dione (U.S. Pat. No. 4,436,745, U.S. Pat. No. 4,438,272);

16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);

17. spiro[imidazolidine-4,5'(6H)-quinoline]2,5-dione-3'-chloro-7',8'-dihydro-7'-methyl-(5'-cis)(U.S. Pat. No. 5,066,659);

18. (2S,4S)-6-fluoro-2',5'-dioxospiro(chroman4,4'-imidazolidine)-2-carboxamide (U.S. Pat. No. 5,447,946); and 19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula I

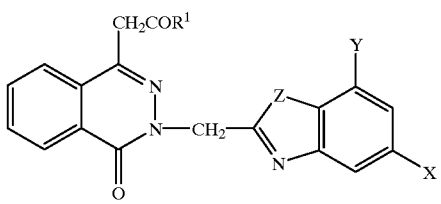

or a pharmaceutically acceptable salt thereof, wherein
Z is O or S;
$R^1$ is hydroxy or a group capable of being removed in vivo to produce a compound of formula I wherein $R^1$ is OH; and
X and Y are the same or different and are selected from hydrogen, trifluoromethyl, fluoro, and chloro.

A preferred subgroup within the above group of compounds includes numbered compounds 1, 2, 3, 4, 5, 6, 9, 10, and 17, and the following compounds of Formula I:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7-dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=CF$_3$; Y=H];

25. 3,4-dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred.

The aldose reductase compounds of this invention are readily available or can be easily synthesized by those skilled in the art using conventional methods of organic synthesis particularly in view of the pertinent patent specification descriptions.

Some of the aldose reductase compounds of this invention have asymmetric carbon atoms and therefore are enantiomers or diastereomers. Diasteromeric mixtures can be separated into their individual diastereomers on the basis of their physical chemical differences by methods known per se, for example, by chromatography and/or fractional crystallization.

Some of the aldose reductase compounds of this invention are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

Some of the compounds of this invention are basic and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, some of the compounds of this invention form hydrates or solvates and they are also within the scope of the invention.

The activity and thus utility of the compounds of the present invention as medical agents in providing protection from ischemic damage to non-cardiac tissue in a mammal can be further demonstrated by the activity of the compounds in the in vitro assay described herein-below. The assay also provides a means whereby the activities of the compounds of this invention can be compared with the activities of other known compounds. The results of these comparisons are useful for determining dosage levels in mammals, including humans, for inducing protection from ischemia.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose). While not wishing to be bound by any particular theory or mechanism, it is believed that an aldose reductase inhibitor, by inhibiting aldose reductase, prevents or reduces ischemic damage as described hereinafter.

When the supply of oxygenated blood to a tissue is interrupted or slowed down (ischemia) the cells in the oxygen-deficient tissue derive their energy (ATP) from glucose via glycolysis (which does not require the presence of oxygen) (see chart below). Glycolysis requires a supply of glucose and NAD$^+$ and in an ischemic tissue the length of time glycolysis can be maintained becomes sensitive to the supply of glucose and NAD$^+$. However, glucose is also used up by aldose reductase (AR) to make sorbitol, and sorbitol dehydrogenase (SDH) also utilizes NAD$^+$ but does not produce an increase in ATP. Thus, it follows that preventing or retarding glucose use by aldose reductase, and NAD$^+$ use by SDH with an aldose reductase inhibitor (ARI) (an aldose reductase inhibitor blocks the use of NAD$^+$ by SDH by blocking the production of sorbitol and thus sorbitol's consequent reaction with SDH and use of NAD$^+$) will enhance or prolong the ability of ischemic tissue to carry out glycolysis i.e., to produce energy in the absence of oxygen and in turn enhance and prolong the survival of the cells in the tissue. Since inhibition of aldose reductase will retard depletion of the tissue's glucose and NAD$^+$, an aldose reductase inhibitor is an effective anti-ischemic agent.

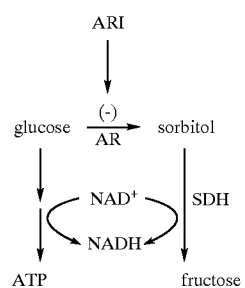

Again, the activity of an aldose reductase inhibitor can be determined by the amount of aldose reductase inhibitor that is required to lower tissue sorbitol and thus lower tissue fructose according to the following assay.

Male Sprague-Dawley rats are rendered diabetic by injection of streptozocin at 55 mg/kg, i.v., in pH 4.5 citrate buffer. They are fed ad libitum in controlled conditions of housing, temperature and lighting. After five weeks of diabetes, the rats are anesthetized with an overdose of pentobarbital, and tissues are rapidly removed and analyzed for sorbitol and fructose.

Sorbitol levels are analyzed according to the method of Donald M. Eades et al., "Rapid Analysis of Sorbitol, Galactitol, Mannitol and Myoinositol Mixtures From Biological Sources", *Journal of Chromatography*, 490, 1–8, (1989).

Fructose in rat tissues is enzymatically measured using a modification of the method of Ameyama (*Methods in Enzymology*, 89:20–29, 1982), in which ferricyanide was replaced by resazurin, a dye that is reduced to the highly fluorescent resorufin. The amount of resorufin fluorescence is stoichiometric with the amount of fructose oxidized by fructose dehydrogenase. The assay contains 0.1 ml neutralized 6% perchloric acid nerve extract in a final volume of 1.5 ml. Following incubation for 60 minutes at room temperature in a closed drawer, sample fluorescence is determined at excitation=560 nm, emission=580 nm with slits of 5 mm each in a Perkin-Elmer model 650-40 fluorescence spectrophotometer. Fructose concentrations are calculated by comparison with a series of known fructose standards.

The aldose reductase inhibitor compounds of this invention are thus useful in reducing or minimizing damage effected directly to any tissue that may be susceptible to ischemia/reperfusion injury (e.g., brain, lung, kidney, liver, gut, skeletal muscle, pancreas, spleen, or retina tissue) as the result of an ischemic event (e.g., arterial embolism). The active compound is therefore usefully employed prophylactically to prevent, i.e. (prospectively or prophylactically) to blunt or stem, tissue ischemia (e.g., skeletal muscle ischemia) in patients who are at risk for peripheral muscle ischemia (e.g., patients with peripheral vascular disease).

The aldose reductase inhibitor compounds of this invention are particularly well suited to the treatment of diabetic patients because of increased metabolism through aldose reductase in the diabetic state. The compounds of this invention are also well suited for prophylactic use with non-diabetic patients who have actually suffered or who are considered at risk of suffering from ischemic events (e.g., patients undergoing surgical procedures or patients with peripheral vascular diseases).

Administration of the compounds of this invention can be via any method which delivers the aldose reductase inhibitors to the desired tissue. These methods include topical, oral routes, parenteral, intraduodenal routes, etc.

Thus, for example, in one mode of administration the aldose reductase inhibitor of this invention may be administered just prior to major surgery requiring general anesthesia (e.g., within twenty-four hours of surgery) where there is risk of ischemia e.g., gastric ischemia. In an alternative exemplary mode, the compounds may be administered subsequent to transplant surgery (e.g., within twenty-four hours after surgery) where there is risk of ischemia in a transplanted tissue. The compounds of this invention may also be administered in a chronic daily mode. In any event the amount and timing of compound(s) administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the effect that the attending physician considers appropriate for the patient. In considering the degree of aldose reductase inhibitor activity desired, the physician must balance a variety of factors such as the target tissue and severity of the disease/condition age of the patient.

An amount of the aldose reductase inhibitor of this invention that is effective for non-cardiac ischemic protection is used. Typically, an effective dosage for the aldose reductase inhibitors of this invention is in the range of about 0.1 mg/kg/day to 100 mg/kg/day in single or divided doses, preferably 0.1 mg/kg/day to 20 mg/kg/day in single or divided doses.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug (e.g., due to age or surgical state). For certain tissues such as the eye, topical administration may also be suitable.

Some aldose reductase inhibitors do not provide effective concentration in the brain when dosed orally and are preferably administered by a route that allows them to reach brain tissue in sufficient concentration e.g., intracranially or topically. Those compounds that do not readily cross the blood/brain barrier, may be determined by standard assays such as high pressure liquid chromatography analysis of brain tissue extracts, e.g., *Pharmaceutical Research*, 8: 1511–1515, 1991. "Pharmacokinetics of Zopolrestat, a Carboxylic Acid Aldose Reductase Inhibitor, in Normal and Diabetic Rats".

The compounds of the present invention are generally administered in the form of a pharmaceutical composition comprising at least one aldose reductase inhibitor together with a pharmaceutically acceptable vehicle or diluent. Thus, the compounds can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compound of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Transdermal or intracranial (e.g., topical) compositions may be prepared by those skilled in the art.

Methods of preparing various pharmaceutical compositions with a certain amount of active ingredient are known, or will be apparent in light of this disclosure, to those skilled in this art. For examples, see *Remington's Pharmaceutical Sciences*, Mack Publishing Company, Easter, Pa., 15th Edition (1975).

Pharmaceutical compositions according to the invention may contain 0.01%–95% of the compound(s) of this invention, preferably 1%–70%. In any event, the composition or formulation to be administered will contain a quantity of a compound(s) according to the invention in an amount effective to treat the signs of the subject being treated, i.e., protection from non-cardiac ischemic damage.

EXAMPLE 1

Male Sprague-Dawley rats were rendered diabetic by injection of streptozocin at 55 mg/kg, i.v., in pH 4.5 citrate buffer. They were fed ad libitum in controlled conditions of housing, temperature and lighting. After five weeks of diabetes, the rats were anesthetized with an overdose of pentobarbital, and tissues were rapidly removed and analyzed for sorbitol and fructose by methods cited above.

Sorbitol levels were analyzed according to the method of Donald M. Eades et al., "Rapid Analysis of Sorbitol, Galactitol, Mannitol and Myoinositol Mixtures From Biological Sources", *Journal of Chromatography*, 490, 1–8, (1989).

Fructose in rat tissues was enzymatically measured using a modification of the method of Ameyama (*Methods in Enzymology*, 89, 1982), in which ferricyanide was replaced by resazurin, a dye that is reduced to the highly fluorescent resorufin. The amount of resorufin fluorescence is stoichiometric with the amount of fructose oxidized by fructose dehydrogenase. The assay contained 0.1 ml neutralized 6% perchloric acid nerve extract in a final volume of 1.5 ml. Following incubation for 60 minutes at room temperature in a closed drawer, sample fluorescence was determined at excitation=560 nm, emission=580 nm with slits of 5 mm each in a Perkin-Elmer model 650-40 fluorescence spectrophotometer. Fructose concentrations were calculated by comparison with a series of known standards containing 0 to 200 ng fructose per assay.

Table 1 details the lowered tissue fructose in a variety of tissues and thus the inhibition of aldose reductase and consequently the anti-ischemic activity of the aldose reductase inhibitor.

TABLE 1

Effects of zopolrestat (ZOP) (50 mg/kg bw/day) on Retina, Sciatic nerve and Lens sorbitol (Sor) and fructose (Fru) levels (nmole/g) in rats with diabetes of 5 weeks duration

|  | Retina | | Sciatic Nerve | | Lens | |
| --- | --- | --- | --- | --- | --- | --- |
|  | Sor | Fru | Sor | Fru | Sor | Fru |
| Control | 126 | 76 | 159 | 814 | 436 | 983 |
|  | (75) | (14) | (55) | (197) | (73) | (151) |
| +ZOP | 122 | 55 | 24 | 179 | 249 | 580 |
|  | (59) | (7.5) | (11) | (60) | (105) | (115) |
| Diabetic | 1409 | 1289 | 1863 | 5815 | 37006 | 12676 |
|  | (412) | (178) | (623) | (1711) | (6964) | (1261) |
| +ZOP | 580 | 960 | 170 | 1217 | 7894 | 9724 |
|  | (195) | (166) | (85) | (253) | (1856) | (1362) |

* Mean ± SD (N = 8–13)
( ) numbers in parenthesis are standard deviation

EXAMPLE 2

Effect of an Aldose Reductase Inhibitor on Survival in a Murine Model of Endotoxic Shock Methods The test compound was a compound of Formula I as described above wherein Z is S and X and Y are both fluoro.

Male Balb/c mice (23–24 g) were divided into groups of 10 and dosed orally with vehicle (0.5% carboxymethylcellulose in water) or vehicle containing 10, 30 or 100 mg/kg of the test compound.

Twenty minutes after dosing with the test compound, shock was induced by the intraperitoneal injection of lipopolysaccharide (LPS) (*E. coli* 0111:B4, 8.5 mg/kg). Thereafter, the test compound was dosed daily. Survival was monitored at intervals up to 72 hours after induction of shock.

TABLE 2

|  | Percent Mortality | | | |
| --- | --- | --- | --- | --- |
|  | Day 0 | Day 1 | Day 2 | Day 3 |
| Vehicle | 0 | 0 | 60 | 60 |
| 10 mg/kg | 0 | 10 | 40 | 50 |
| 30 mg/kg | 0 | 0 | 20 | 20 |
| 100 mg/kg | 0 | 10 | 80 | 80 |

In the vehicle group 60% of the animals died by 2 days after injection of LPS. The test compound reduced mortality at 10 and 30 mg/kg/day with 30 mg/kg/day being the optimal dose (20% mortality in this group).

Table 2 details the protection from LPS induced shock by an exemplary aldose reductase inhibitor. Protection from endotoxin induced shock is predictive for ischemic protection as disclosed in FIG. 2 of *Clinical Microbiology Review*, January 1993, p. 57–68, Vol. 6, No. 1.

It should be understood that the invention is not limited to the particular embodiments described herein, but that various changes and modifications may be made without departing from the spirit and scope of this novel concept as defined by he following claims.

What is claimed is:

1. A method of treating non-cardiac tissue damage, resulting from ischemia comprising administering to a mammal an amount of zopolrestat effective at reducing non-cardiac ischemic damage, with the proviso that transient cerebral ischemia is not included.

2. A method as recited in claim 1 wherein the tissue is brain, liver, kidney, lung, gut, skeletal muscle, spleen, pancreas, retina tissue or intestinal tissue.

3. A method as recited in claim 2 wherein said mammal is a human.

4. A method as recited in claim 3 wherein said tissue is brain tissue.

5. A method as recited in claim 3 wherein said tissue is liver tissue.

6. A method as recited in claim 3 wherein said tissue is kidney tissue.

7. A method as recited in claim 3 wherein said tissue is lung tissue.

8. A method as recited in claim 3 wherein said tissue is gut tissue.

9. A method as recited in claim 3 wherein said tissue is skeletal muscle tissue.

10. A method as recited in claim 3 wherein said tissue is spleen tissue.

11. A method as recited in claim 3 wherein said tissue is pancreas tissue.

12. A method as recited in claim 3 wherein said tissue is retina tissue.

13. A method as recited in claim 3 wherein the effective amount of zopolrestat is about 0.1 mg/kg/day to about 100 mg/kg/day.

14. A method as recited in claim 13 wherein said zopolrestat is administered prophylactically.

15. A method as recited in claim 13 wherein said zopolrestat is administered chronically.

16. A method as recited in claim 3 wherein the tissue is skeletal muscle or retina tissue.

17. A method as recited in claim 3 wherein said tissue is intestinal tissue.

18. A method as recited in claim 3 wherein the human has diabetes.

* * * * *